United States Patent
Suzuki et al.

(10) Patent No.: US 6,667,412 B1
(45) Date of Patent: Dec. 23, 2003

(54) NITRILE COMPOUND

(75) Inventors: Yuichi Suzuki, Ibaraki (JP); Noboru Yamamoto, Ibaraki (JP); Koki Kawano, Ibaraki (JP); Teiji Kimura, Ibaraki (JP); Koichi Ito, Ibaraki (JP); Satoshi Nagato, Chiba (JP); Yoshihiko Norimine, Ibaraki (JP); Yoichi Iimura, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/914,349

(22) PCT Filed: Mar. 14, 2000

(86) PCT No.: PCT/JP00/01530

§ 371 (c)(1),
(2), (4) Date: Aug. 27, 2001

(87) PCT Pub. No.: WO00/55122

PCT Pub. Date: Sep. 21, 2000

(30) Foreign Application Priority Data

Mar. 16, 1999 (JP) .......................... 11-070613

(51) Int. Cl.[7] ............................ C07C 255/36
(52) U.S. Cl. ............................ 558/406; 558/410
(58) Field of Search .................. 558/406, 410

(56) References Cited

U.S. PATENT DOCUMENTS 2,935,512 A * 5/1960 Redel ................ 546/296
4,940,780 A    7/1990 Seitz et al.

FOREIGN PATENT DOCUMENTS

| EP | 261073 | | 3/1988 | |
|----|--------|---|--------|---|
| EP | 0261073 | A2 | 3/1988 | |
| EP | 505122 | | 9/1992 | |
| EP | 805147 | | 11/1997 | |
| EP | 1 099 692 | A1 | 5/2001 | |
| FR | 1295305 | * | 5/1962 | ............ 558/406 |
| GB | 1367677 | | 9/1974 | |
| GB | 1 377 209 | A | 12/1974 | |
| JP | 5490160 | | 7/1979 | |
| JP | 54090160 | A | 7/1979 | |
| JP | 62126160 | A | 6/1987 | |
| JP | 62126160 | | 6/1987 | |
| JP | 63156763 | | 6/1988 | |
| WO | 9532947 | | 12/1995 | |
| WO | WO9532947 | | 12/1995 | |
| WO | 9729080 | | 8/1997 | |
| WO | WO9729080 | | 8/1997 | |
| WO | 0005210 | | 2/2000 | |
| WO | WO0005210 | | 2/2000 | |

OTHER PUBLICATIONS

C.A. 97:87060 Kis–Tamas HU 179635 Nov. 1982 R.N. 79341–72–3.*

Database CA Online! Chemical Abstracts Service, Columbus, Ohio, US; Wang, Duhu et al: "Synthesis of 1–acylbenzimidazole and 3–acyl–2–thiothiazolidone derivative" retrieved from STN Database accession No. 114:122168, XP002209450, *compound with rn:92250–60–7*, *abstract* & Gaodeng Xuexiao Huaxue Xuebao (1990), 11(7), 756–8.

Dababase CA Online! Chemical Abstracts Service, Columbus, Ohio, US; Julia, Marc et al: "3–Arylpiperidines. I. N–substituted 3–phenylpiperidines" retrieved from STN Database, accession No. 69:77078, XP002209451, *compound with rn:19735–09–2*, *abstract* & Bull. Soc. Chim. Fr. (1968), (3), 987–99.

Database Crossfire Beilstein Online! Beilstein Institut zur Foerderung der Chemischen Wissenschaften, Frankfurt am Main, DE; Database accession No. brn. 2581933, XP002208055, *2–cyano–2–phenyl–pentanoic acid and methyl 2–cyano–2–phenyl–pentanoate* & Knabe, J.; Junginger, H.: Pharat, Pharmazie, GE; 27; 1972; 43–447.

Database Crossfire Beilstein Online! Beilstein Institut zur Foerderung der Chemischen Wissenschaften, Frankfurt am Main, DE; Database accession No. brn 2052871, XP002208056, *3–cyano–3–phenyl–pentanoic acid*, *abstract*, Knabe, J.; Koch, W.: Arpmas; Arch. Pharm. (Weinheim Ger.); GE; 305; 1972; 757–765.

Database Crossfire Beilstein Online! Beilstein Institut zur Forderung der Chemischen Wissenschaften, Frankfurt am Main, DE; Database accession No. brn 2259278, XP002208057, *2–cyano–2–phenyl–propionic acid*, *abstract*, Pifferi, G. et al.: FRPSAX; Farmaco Ed. Sci.; IT; 17; 1962; 882–893.

(List continued on next page.)

*Primary Examiner*—Robert Gerstl
(74) *Attorney, Agent, or Firm*—Birch, Stewart, Kolasch & Birch, LLP

(57) ABSTRACT

The present invention provides a novel nitrile compound useful as an intermediate for the production of, for example, N,N-substituted cyclic amine derivatives or phenylacetonitrile derivatives that are useful as a medicine. Specifically it provides a nitrile carboxylic acid compound, nitrile ester compound and nitrile alcohol compound. That is, it provides a nitrile compound represented by the following formula (I):

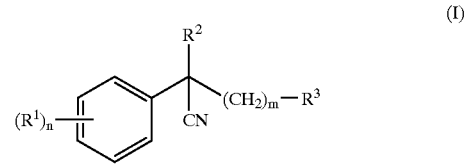

(I)

wherein $R^1$ and $R^2$ means substituents; m means 0 or an integer of from 1 to 6; n means 0 or an integer of from 1 to 5; and $R^3$ means carboxyl group, a lower alkoxycarbonyl group or hydroxymethyl group.

8 Claims, No Drawings

OTHER PUBLICATIONS

Database Crossfire Beilstein Online! Beilstein Institut zur Forderung der Chemischen Wissenschaften, Frankfurt am Main, DE; Database accession No. brn 2051088, XP002208058, *3-cyano-3-phenyl-butyric acid*, *abstract*, Knabe, J.; Koch, W.: Arpmas; Arch. Pharm. (Weinheim Ger.); GE; 305; 1972; 849-854.

Database Crossfire Beilstein Online! Beilstein Institut zur Forderung der Chemischen Wissenschaften, Frankfurt am Main, DE; Database accession No. brn 2053435, XP002208059, *4-cyano-4-phenyl-hexanoic acid*, *abstract*, Salmon-Legagneur; Neveu: Bscfas; Bull. Soc. Chim. Fr.; 1953; 70;74.

Database Crossfire Beilstein Online! Beilstein Institut zur Foerderung der Chemischen Wissenschaften, Frankfurt am Main, DE; Database accession No. brn: 2585903, XP002208060, *3-cyano-3-methyl-2-phenyl-pentanoic acid*, *abstract*, Fujita et al.: ABCHA6; Agric. Biol. Chem.; 30; 1966; 1280, 1283.

Database Crossfire Beilstein Online! Beilstein Institut zur Forderung der Chemischen Wissenschaften, Frankfurt am Main, DE; Database accession No. brn 238367, XP002208061, *2-benzo'1, 3!dioxol-5-yl-2-cyano-butyric acid*, *abstract*, Niederl; Ziering: Jacsat; J. Amer. Chem. Soc.; 64; 1942; 2486.

Database Crossfire Beilstein Online ! Beilstein Institut zur Forderung der Chemischen Wissenschaften, Frankfurt am Main, DE; Database accession No. brn 2581030, XP002208062, *2-(4-chloro-phenyl)-2-cyano-propionic acid*, *abstract*, Cramer; Kampe: Jacsat; J. Amer. Chem. Soc.; 87; 1965; 1115, 1118.

* cited by examiner

NITRILE COMPOUND

This application is the national phase under 35 U.S.C. §371 of PCT International Application No. PCT/JP00/01530 which has an International filing date of Mar. 14, 2000, which designated the United States of America and was not published in English.

TECHNICAL FIELD

The present invention relates to a novel nitrile compound useful as an intermediate for the production of, for example, N,N-substituted cyclic amine derivatives useful as medicine as disclosed in WO00/05210 (published Feb. 3, 2000) or phenylacetonitrile derivatives useful as medicine as disclosed in JP-A-63-156,763 (EP-271,013). More particularly, it relates to a nitrile carboxylic acid compound, nitrile ester compound and nitrile alcohol compound.

PRIOR ART

N,N-Substituted cyclic amine derivatives disclosed in WO00/05210 (published Feb. 3, 2000) or phenylacetonitrile derivatives disclosed in JP-A 63-156763 (EP-271013), for example, have been synthesized by reductive amination using aldehyde derivatives and amine derivatives.

Although the above reductive amination is an excellent reaction from the viewpoint of yield, the aldehyde derivatives that serve as a raw material have various problems. That is, they have very high reactivity so that their stability is poor (oxidation, decomposition, polymerization etc.), by-products that are difficult to purify tend to occur depending on the reaction conditions, generally they are expensive, and the like.

DISCLOSURE OF THE INVENTION

Accordingly, the present inventors have made extensive studies paying attention to novel compounds having utility from the viewpoints of raw material stability, production costs, manipulability (workability), final product purity and so forth. As a result, they have found out that novel nitrile compounds, more particularly nitrile carboxylic acid compounds, nitrile ester compounds and nitrile alcohol compounds can solve the above problems simultaneously, thereby achieving the present invention.

Therefore, an object of the present invention is to provide novel intermediates useful for the production of fine chemicals such as medicines.

The present invention is a nitrile compound represented by the following formula (I).

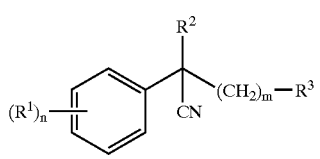

(I)

Wherein $R^1$s are the same as or different from each other and each means hydrogen atom, a halogen atom, hydroxyl group, a lower alkyl group, a lower cycloalkyl group, a lower alkoxy group, a lower alkoxyalkoxy group, a halogenated lower alkyl group, a hydroxy-lower alkyl group, a cyano-lower alkyl group, a halogenated lower alkoxy group, a hydroxy-lower alkoxy group, a cyano-lower alkoxy group, a lower acyl group, nitro group, an optionally substituted amino group, an optionally substituted carbamoyl group, an optionally substituted sulfamoyl group, mercapto group or a lower alkylthio group;

$R^2$ means a lower alkyl group or a lower cycloalkyl group, and two $R^1$s may combine to form an aliphatic ring, an aromatic ring, a hetero ring or an alkylenedioxy ring;

n means 0 or an integer of from 1 to 5;

m means 0 or an integer of from 1 to 6; and $R_3$ means carboxyl group, a lower alkoxycarbonyl group, a phenyloxycarbonyl group optionally having a substituent, a phenyl-lower alkylenyl group optionally having a substituent, or hydroxymethyl group.

In the above definitions, the term "halogen atom" specifically means, for example, fluorine, chlorine, bromine or iodine.

The term "lower alkyl group" means an alkyl group having 1 to 6 carbon atoms and specifically includes, for example, straight chain or branched alkyl groups, such as methyl group, ethyl group, n-propyl group, i-propyl group, n-butyl group, i-butyl group, t-butyl group, n-pentyl group, i-pentyl group, neopentyl group, hexyl group, 1-methylpropyl group, 1-methylbutyl group and 2-methylbutyl group. The term "lower alkylenyl group" means an alkylene chain composed of the above-mentioned alkyl group, including, for example, methylene group, ethylene group, propylene group and so forth.

The term "lower cycloalkyl group" means a cyclic alkyl group having 3 to 8 carbon atoms and specifically includes, for example, cyclopropyl group, cyclobutyl group, cyclopentyl group, cyclohexyl group, cycloheptyl group, cyclooctyl group and so forth.

The term "lower alkoxy group" means a group resulting from a combination of the above-mentioned lower alkyl group with oxygen atom, and specifically includes straight chain or branched alkoxy groups, for example, methoxy group, ethoxy group, n-propoxy group, i-propoxy group, n-butoxy group, i-butoxy group, t-butoxy group, pentyloxy group, hexyloxy group and so forth.

The term "lower alkoxyalkoxy group" means a group resulting from a combination of the above-mentioned alkoxy group with another lower alkoxy group, and specifically includes, for example, methoxymethoxy group, methoxyethoxy group, methoxypropoxy group, ethoxymethoxy group, ethoxyethoxy group, ethoxypropoxy group, propoxymethoxy group, propoxyethoxy group, propoxypropoxy group and so forth.

The term "halogenated lower alkyl group" means a group resulting from combination of the above-mentioned lower alkyl group with one or more halogen atoms, which may be the same as or different from, and specifically includes, for example, chloromethyl group, dichloromethyl group, trichloromethyl group, fluoromethyl group, difluoromethyl group, trifluoromethyl group, fluoroethyl group, difluoroethyl group, trifluoroethyl group and so forth.

The term "hydroxy lower alkyl group" means a group resulting from combination of the above-mentioned alkyl group with one or more hydroxyl groups, and specifically includes, for example, hydroxymethyl group, hydroxyethyl group, 2,3-dihydroxypropyl group and so forth.

The term "cyano lower alkyl group" means a group resulting from combination of the above-mentioned lower alkyl group with one or more cyano groups, and specifically includes, for example, cyanomethyl group, cyanoethyl group, cyanopropyl group and so forth.

The terms "halogenated lower alkoxy group", "hydroxy lower alkoxy group", and "cyano lower alkoxy group" mean a group resulting from a combination of the above-mentioned halogenated lower alkyl group with an oxygen atom, a group resulting from a combination of the above-mentioned hydroxy lower alkyl group with an oxygen atom, and a group resulting from a combination of the above-mentioned cyano lower alkyl group with an oxygen atom, respectively.

The term "lower acyl group" means a straight chain or branched acyl group derived from a fatty acid having 1 to 6 carbon atoms, and specifically includes, for example, formyl group, acetyl group, propionyl group, butyryl group, isobutyryl group, valeryl group, isovaleryl group, pivaloyl group, hexanoyl group and so forth.

The term "optionally substituted amino group" means an amino group whose nitrogen atom may be substituted with a lower alkyl group or the like. It also includes the case where the nitrogen atom is a part of a cyclic amine. Specific examples thereof include amino group (—NH$_2$), methylamino group (—NHCH$_3$), dimethylamino group (—N(CH$_3$)$_2$), ethylamino group (—NHC$_2$H$_5$), diethylamino group (—N(C$_2$H$_5$)$_2$), methylethylamino group (—N(CH$_3$)C$_2$H$_5$), pyrrolidinyl group, pyrazolinyl group, piperidinyl group, piperazinyl group, 4-morpholinyl group, 4-thiomorpholinyl group and so forth.

The term "optionally substituted carbamoyl group" means a carbamoyl group whose nitrogen atom may be substituted with a lower alkyl group or the like, and also includes the case where the nitrogen atom is apart of a cyclic amine. Specific examples thereof include carbamoyl group (—CONH$_2$), N-methylcarbamoyl group (—CONHCH$_3$), N,N-dimethylcarbamoyl group (—CON(CH$_3$)$_2$), N-ethylcarbamoyl group (—CONHC$_2$H$_5$), N,N-diethylcarbamoyl group (—CON(C$_2$H$_5$)), N-methyl-N-ethylcarbamoyl group (—CON(CH$_3$)C$_2$H$_5$), 1-pyrrolidinylcarbonyl group, 1-pyrazolinylcarbonyl group, 1-piperidinylcarbonyl group, 1-piperazinylcarbonyl group, 4-morpholinylcarbonyl group, 4-thiomorpholinylcarbonyl group and so forth.

The term "optionally substituted sulfamoyl group" means a sulfamoyl group whose nitrogen atom may be substituted with a lower alkyl group or the like, and includes also the case where the nitrogen atom is apart of a cyclic amine. Specific examples thereof include sulfamoyl group (—SO$_2$NH$_2$), N-methylsulfamoyl group (—SO$_2$NHCH$_3$), N,N-dimethylsulfamoyl group (—SO$_2$N(CH$_3$)$_2$), N-ethylsulfamoyl group (—SO$_2$NHC$_2$H$_5$), N,N-diethylsulfamoyl group (—SO$_2$N(C$_2$H$_5$)$_2$), N-methyl-N-ethylsulfamoyl group (—SO$_2$N(CH$_3$)C$_2$H$_5$), 1-pyrrolidinylsulfonyl group, 1-pyrazolinylsulfonyl group, 1-piperidinylsulfonyl group 1-piperazinylsulfonyl group, 4-morpholinylsulfonyl group, 4-thiomorpholinylsulfonyl group and so forth.

The term "lower alkylthio group" means a group resulting from the above-mentioned lower alkyl group with sulfur atom, and specifically includes, for example, methylthio group (—SCH$_3$), ethylthio group (—SC$_2$H$_5$) and so forth.

Furthermore, specific examples in which two R$^1$s combine to form an aliphatic ring include, for example, cyclopentane ring, cyclohexane ring, cycloheptane ring, cyclooctane ring and so forth. Those in which two R$^1$s combine to form an aromatic ring include, for example, benzene ring and so forth. Those in which two R$^1$s combine to form a hetero ring include, for example, furan ring, thiophene ring, pyrrole ring, imidazole ring, triazole ring, tetrazole ring, oxazole ring, thiazole ring, pyridine ring, pyrazine ring, pyrimidine ring, tetrahydrofuran ring, tetrahydropyran ring, tetrahydrothiophene ring, pentamethylene sulfide ring, dioxane ring, dioxolane ring, pyrrolidine ring, piperidine ring, piperazine ring, morpholine ring, thiomorpholine ring and so forth. Those in which two R$^1$s combine to form an alkylenedioxy ring include, for example, methylenedioxy group, ethylenedioxy group, propylenedioxy group and so forth.

The term "lower alkoxycarbonyl group" means a group resulting from a combination of the above-mentioned lower alkoxy group with carbonyl group, and specifically includes, for example methoxycarbonyl group (—COOCH$_3$), ethoxycarbonyl group (—COOC$_2$H$_5$) etc.

The term "phenyl group optionally having a substituent" means a phenyl group that may be substituted with a lower alkyl group, a lower alkoxy group, a halogen atom, cyano group etc.

The nitrile compound (I) of the present invention may more specifically include the following compounds. However, the present invention should not be limited thereto.

(1) 4-Cyano-5-methyl-4-phenylhexanoic acid,
(2) methyl 4-cyano-5-methyl-4-phenylhexanoate,
(3) ethyl 4-cyano-5-methyl-4-phenylhexanoate,
(4) 4-cyano-5-methyl-4-phenylhexanol,
(5) 4-cyano-5-methyl-4-(4-methoxyphenyl)hexanoic acid,
(6) 4-cyano-5-methyl-4-(3,4-dimethoxyphenyl)hexanoic acid,
(7) 4-cyano-5-methyl-4-(3,4,5-trimethoxyphenyl)hexanoic acid,
(8) 4-cyano-5-methyl-4-(4-chlorophenyl)hexanoic acid,
(9) 4-cyano-5-methyl-4-(3,4-dichlorophenyl)hexanoic acid,
(10) 4-cyano-5-methyl-4-(3,4,5-trichlorophenyl)hexanoic acid,
(11) 4-cyano-5-methyl-4-(2-trifluoromethylphenyl)hexanoic acid,
(12) 4-cyano-5-methyl-4-(3-trifluoromethylphenyl)hexanoic acid,
(13) 4-cyano-5-methyl-4-(4-trifluoromethylphenyl)hexanoic acid,
(14) 4-cyano-5-methyl-4-(3-sulfamoyl-4-methoxyphenyl)hexanoic acid,
(15) 4-cyano-5-methyl-4-(2-fluorophenyl)hexanoic acid,
(16) 4-cyano-5-methyl-4-(3-fluorophenyl)hexanoic acid,
(17) 4-cyano-5-methyl-4-(4-fluorophenyl)hexanoic acid,
(18) 4-cyano-5-methyl-4-(2-cyanophenyl)hexanoic acid,
(19) 4-cyano-5-methyl-4-(3-cyanophenyl)hexanoic acid,
(20) 4-cyano-5-methyl-4-(4-cyanophenyl)hexanoic acid,
(21) 4-cyano-5-methyl-4-(2-chlorophenyl)hexanoic acid,
(22) 4-cyano-5-methyl-4-(3-chlorophenyl)hexanoic acid,
(23) 4-cyano-5-methyl-4-(2-bromophenyl)hexanoic acid,
(24) 4-cyano-5-methyl-4-(3-bromophenyl)hexanoic acid, and
(25) 4-cyano-5-methyl-4-(4-bromophenyl)hexanoic acid.

Subsequently, a general production method for the nitrile compound (I) of the present invention will be described in detail. However, they can be produced by other methods than this.

(1) Where m=0

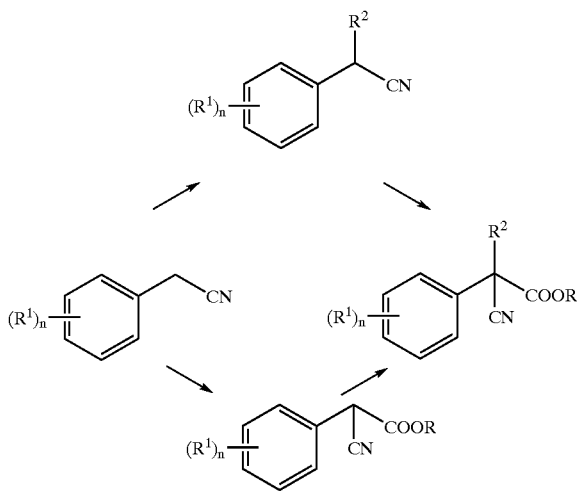

wherein $R^1$, $R^2$ and n have the same meanings as described above; and R means an alcohol residue that constitutes an ester such as a lower alkyl group.

In this method, phenylacetonitrile optionally having a substituent can be converted into the nitrile ester compound of the present invention, by lower alkylating or lower cycloalkylating the methylene group of the phenylacetonitrile and then alkoxycarbonylating the methyne group, or by first alkoxycarbonylating the methylene group and then lower alkylating or lower cycloalkylating. This product can be derived to a nitrile carboxylic acid compound or a nitrile alcohol compound by a conventional method.

(2) Where m=1

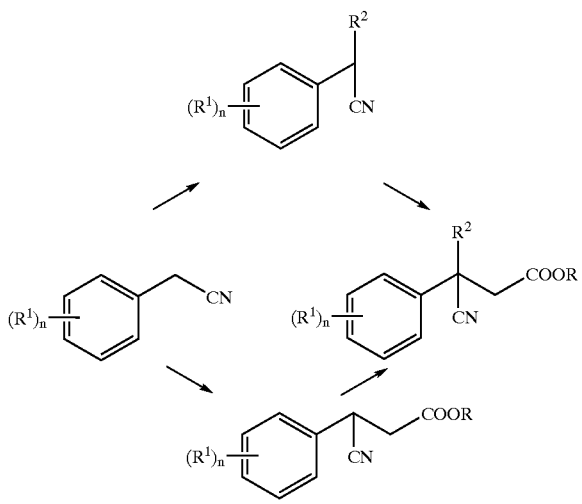

wherein $R^1$, $R^2$ and n have the same meanings as described above; and R means an alcohol residue that constitutes an ester such as a lower alkyl group.

In this method, phenylacetonitrile optionally having a substituent can be converted into the phenyl nitrile ester optionally having a substituent according to the present invention, by reacting the phenylacetonitrile with a halogenated acetic acid ester and then lower alkylating or lower cycloalkylating the product, or by first lower alkylating or lower cycloalkylating the phenylacetonitrile and then reacting the product with a halogenated acetic acid ester. This product can be derived to a nitrile carboxylic acid compound or a nitrile alcohol compound by a conventional method.

(3) Where m=2

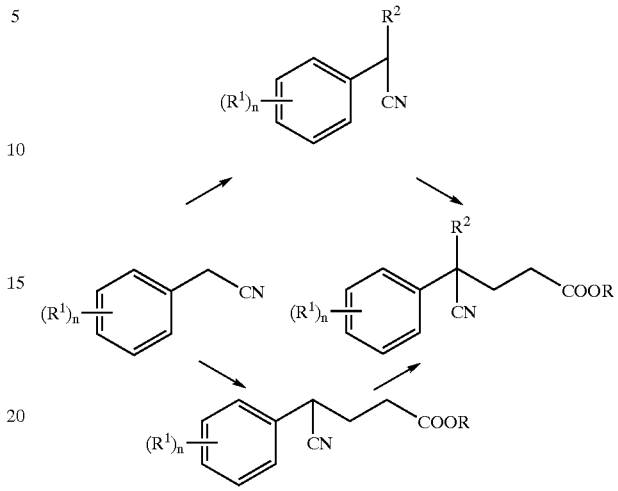

wherein $R^1$, $R^2$ and n have the same meanings as described above; and R means an alcohol residue that constitutes an ester such as a lower alkyl group.

In this method, phenylacetonitrile optionally having a substituent can be converted into the nitrile ester compound of the present invention, by reacting the phenylacetonitrile with an acrylic acid ester or a 3-halogenopropionic acid ester and then lower alkylating or lower cycloalkylating the product, or by first lower alkylating or lower cycloalkylating the phenylacetonitrile and then reacting the product with an acrylic acid ester or a 3-halogenopropionic acid ester. This product can be derived to a nitrile carboxylic acid compound or a nitrile alcohol compound by a conventional method.

(4) Where m=3 to 6

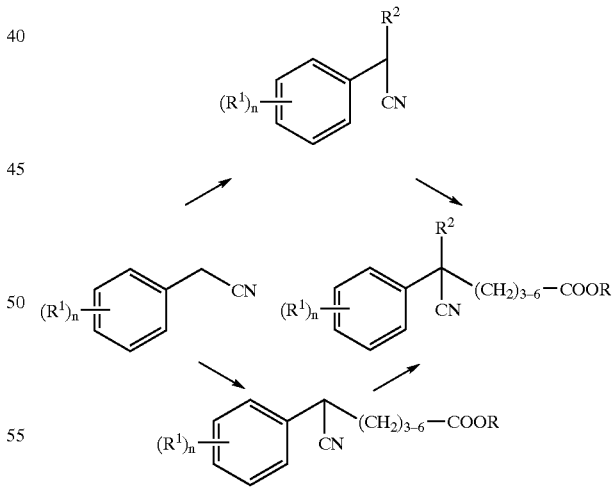

Wherein $R^1$, $R^2$ and n have the same meanings as described above; and R means an alcohol residue that constitutes an ester, such as a lower alkyl group.

In this method, phenylacetonitrile optionally having a substituent can be converted into the nitrile ester compound of the present invention, by reacting the phenylacetonitrile with a corresponding ω-halogenated fatty acid ester and then lower alkylating or lower cycloalkylating the product, or by first lower alkylating or lower cycloalkylating the phenylacetonitrile and then reacting the product with an ω-halogenated fatty acid ester. This product can be derived to a nitrile carboxylic acid compound or a nitrile alcohol compound by a conventional method.

Upon producing the nitrile alcohol compound from the nitrile ester compound or nitrile carboxylic acid compound, reduction can be performed by a conventional method. In this case, the reduction method or reducing agent is not particularly limited. Specifically, for example, borane, lithium aluminum hydride, bis(2-methoxyethoxy)aluminum sodium hydride, sodium triacetoxyborohydride, sodium cyanoborohydride, sodium borohydride, litium borohydride etc. may be utilized.

(5) Where m=2 to 6

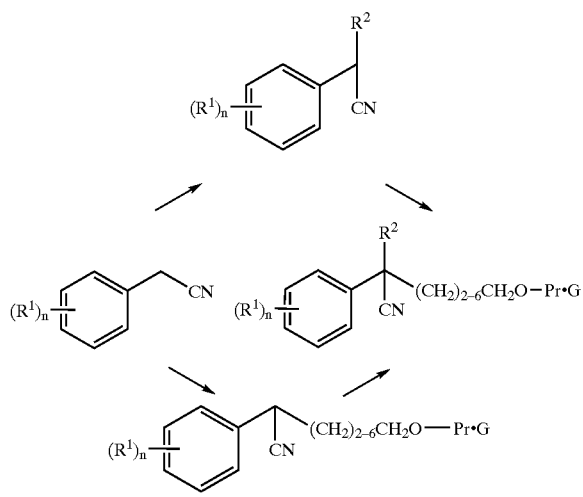

wherein $R^1$, $R^2$ and n have the same meanings as described above; and Pr.G means a protecting group.

In this method, phenylacetonitrile optionally having a substituent can be converted into the nitrile alcohol compound of the present invention, by reacting the phenylacetonitrile with a corresponding ω-halogeno-1-protected hydroxyalkyl and then lower alkylating or lower cycloalkylating the product, or by first lower alkylating or lower cycloalkylating and then reacting the product with an ω-halogeno-1-protected hydroxyalkyl. This product can be deprotected, to give the nitrile alcohol compound of the present invention. Further, this can be oxidized by a conventional method to form the nitrile carboxylic acid compound of the present invention, or further esterified to derive to the nitrile ester compound of the present invention.

The ω-halogeno-1-protected hydroxyalkyl specifically includes; for example, compounds derived from the following alcohol compounds by protecting the hydroxyl group thereof.

1) 2-Chloroethanol
2) 2-Bromoethanol
3) 2-Iodoethaol
4) 3-Chloro-1-propanol
5) 3-Bromo-1-propanol
6) 3-Iodo-1-propanol
7) 4-Chloro-1-butanol
8) 4-Bromo-1-butanol
9) 4-Iodo-1-butanol
10) 5-Chloro-1-pentanol
11) 5-Bromo-1-pentanol
12) 5-Iodo-1-pentanol
13) 6-Chloro-1-hexanol
14) 6-Bromo-1-hexanol
15) 6-Iodo-1-hexanol The protecting groups for their hydroxyl groups are not particularly limited as far as they can be used in ordinary organic syntheses. Specifically, they include, for example, ether type ones, ester type ones, silyl ether type ones and so forth. More specifically, the ether type ones include, for example, methyl ethers, methoxy methyl ethers, methoxy ethoxy methyl ethers, tetrahydropyranyl ethers, allyl ethers, benzyl ethers, triphenylmethyl ethers and so forth. The ester type ones include, for example, formic acid esters, acetic acid esters, benzoic acid esters and so forth. The silyl ether type ones include, for example, trimethylsilyl ethers, t-butyldimethylsilyl ethers and so forth.

Upon oxidizing the nitrile alcohol compounds to form nitrile carboxylic acid compouds, the reaction can be practiced by a conventional method. Specifically, mention may be made of oxidation with manganese dioxide, a permanganate, a permanganate-periodate, chromic acid, silver oxide, ruthenium tetroxide, oxygen, ozone, an organic peracid, or nitric acid, or by electrolytic oxidation.

Esterification of the product can be performed by a conventional method.

As other production methods than (1) to (5) above, also the following methods, for example, can be used.

(6) Method from 2-substituted Phenyl Acetonitrile Derivative as a Starting Material 6-1)

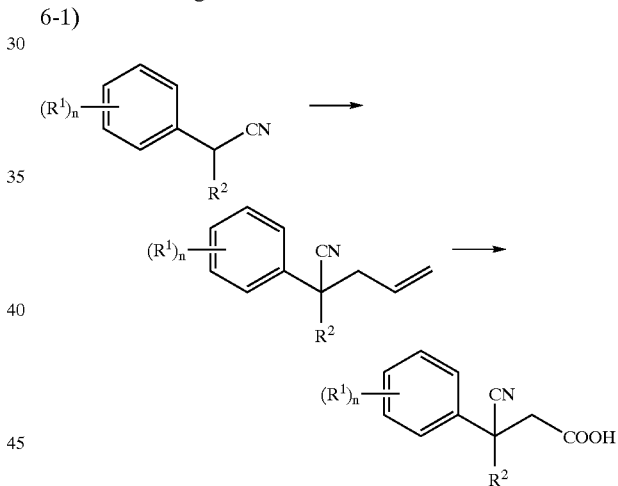

Wherein $R^1$, $R^2$ and n have the same meanings as described above.

In this method, the nitrile carboxylic acid compound of the present invention can be obtained by reacting a 2-substituted phenylacetonitrile derivative and an allyl halide or the like in the presence of a base or Pd(0) catalyst to form an olefin derivative and then oxidizing it.

Here, the allyl halide or the like specifically includes, for example, allyl chloride ($CH_2$=$CHCH_2Cl$), allyl bromide ($CH_2$=$CHCH_2Br$), allyl iodide ($CH_2$=$CHCH_2I$), allyl methanesulfonate ($CH_2$=$CHCH_2OSO_2CH_3$), allyl p-toluenesulfonate ($CH_2$=$CHCH_2OSO_2C_6H_4CH_3$), allyl acetate ($CH_2$=$CHCH_2OCOCH_3$), allyl dimethyl phosphate ($CH_2$=$CHCH_2OPO(OCH_3)_2$), allyl diethyl phosphate ($CH_2$=$CHCH_2OPO(OC_2H_5)_2$) and so forth.

Oxidation of the olefin derivatives can be performed by a conventional method. Specifically, mention may be made of oxidation with an osmium tetroxide-periodate, a permanganate, a permanganate-periodate, chromic acid, ruthenium tetroxide, oxygen, ozone, an organic peracid or nitric acid, or by electrolytic oxidation.

6-2)

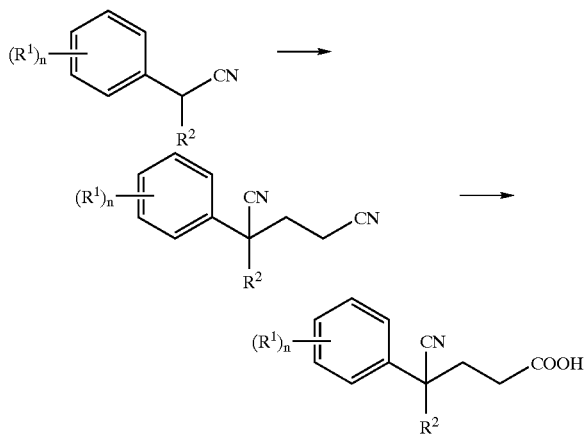

wherein $R^1$, $R^2$ and n have the same meanings as described above.

In this method, the nitrile carboxylic acid compound of the present invention can be obtained by reacting a 2-substituted phenylacetonitrile derivative and allyl cyanide (3-butenenitrile, $CH_2=CHCH_2CN$) to form a dinitrile derivative and then hydrolyzing it.

6-3)

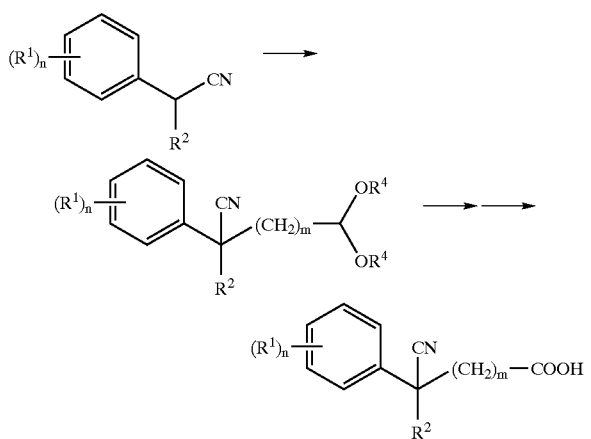

wherein $R^1$, $R^2$, n and m have the same meanings as described above; and $R^4$ means a lower alkyl group, provided that two $R^4$s may combine to form a lower alkylene group.

In this method, the nitrile carboxylic acid compound of the present invention can be obtained by reacting a 2-substituted phenylacetonitrile and an $\omega,\omega$-dialkoxyalkyl halide or the like to form an acetal derivative, hydrolyzing this to obtain an aldehyde derivative, and then oxidizing it.

Here, the $\omega,\omega$-dialkoxyalkyl halide or the like specifically includes, for example, 2-chloro-1,1-dimethoxyethane ($ClCH_2CH(OCH_3)_2$), 2-bromo-1,1-dimethoxyethane ($BrCH_2CH(OCH_3)_2$), 3-chloro-1,1-diethoxypropane ($ClCH_2CH_2CH(OC_2H_5)_2$), 2-bromoethyldioxirane ($BrCH_2CH_2CH(OCH_2)_2$), 2-chloroethyldioxirane ($ClCH_2CH_2CH(OCH_2)_2$), 2-bromoethyldioxane ($BrCH_2CH_2CH(OCH_2CH_2CH_2O)$), 2-chloroethyldioxane ($ClCH_2CH_2CH(OCH_2CH_2CH_2O)$), bromomethyldioxirane ($BrCH_2CH(OCH_2)_2$), chloromethyldioxirane ($ClCH_2CH(OCH_2)_2$), bromomethyldioxane ($BrCH_2CH(OCH_2CH_2CH_2O)$), chloromethyldioxane ($ClCH_2CH(OCH_2CH_2CH_2O)$) and so forth. The $\omega,\omega$-dialkoxyalkyl halide or the like may be $\omega,\omega$-dithioalkoxyalkyl halide or the like.

Oxidation of the aldehyde derivatives can be performed by a conventional method. Specifically, mention may be made of oxidation with manganese dioxide, a permanganate, a permanganate-periodate, chromic acid, silver oxide, ruthenium tetroxide, oxygen, ozone, an organic peracid or nitric acid, or by electrolytic oxidation.

6-4)

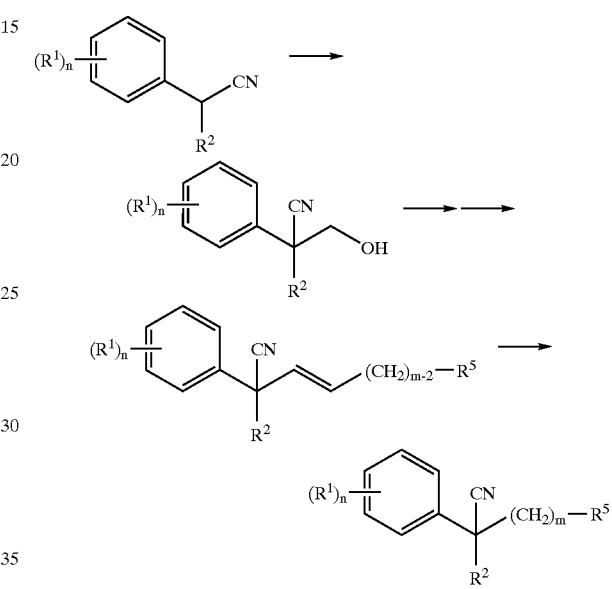

wherein $R^1$, $R^2$, n and m have the same meanings as described above; and $R^5$ means hydroxymethyl group whose hydroxyl group may be protected or a carboxyl group that may be protected.)

The nitrile alcohol compound of the present invention can be obtained by reacting a 2-substituted phenylacetonitrile derivative with formaldehyde in the presence of a base in accordance with Heterocycles, 37(3), 1879–1891, 1994. etc.

This can be oxidized to obtain the nitrile carboxylic acid compound of the present invention. The oxidation may be stopped at the stage of the aldehyde derivative, which may then be subjected to the Wittig reaction to increase the carbon number and further to hydrogenation to obtain a nitrile alcohol compound or nitrile carboxylic acid compound.

The base used herein is not particularly limited but preferably is a strong base, which specifically includes, for example, lithium diisopropylamide, lithium bis (trimethylsilyl)amide, n-butyllithium, sodium amide, lithium amide, sodium hydride, sodium methoxide, sodium ethoxide, potassium t-butoxide, sodium hydroxide, potassium hydroxide and so forth.

Oxidation of the nitrile alcohol compouds can be performed by a conventional method. Specifically, mention may be made of oxidation with manganese dioxide, a permanganate, a permanganate-periodate, chromic acid, silver oxide, ruthenium tetroxide, oxygen, ozone, an organic peracid or nitric acid, or by electrolytic oxidation.

(7) Method Using Phenylacetic Acid Ester Derivative as a Starting Material

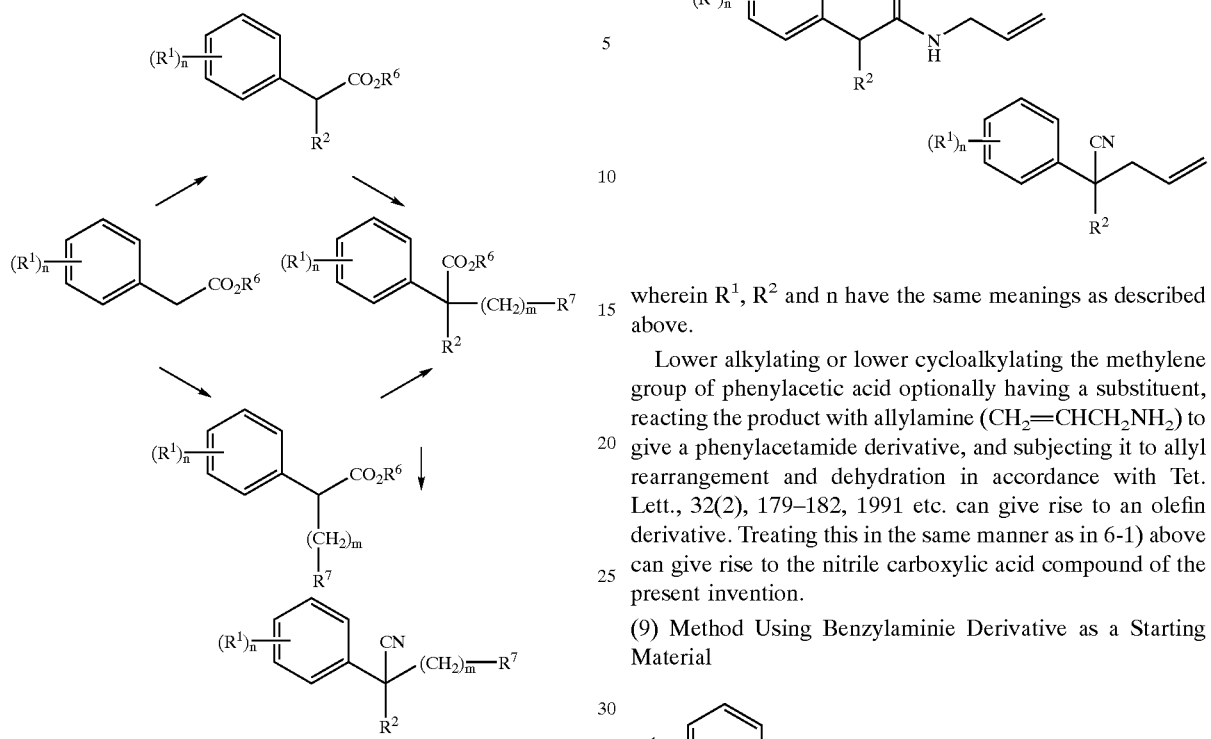

wherein $R^1$, $R^2$, n and m have the same meanings as described above; $R^6$ means hydrogen atom or a lower alkyl group; and $R^7$ means carboxyl group, a lower alkoxycarbonyl group, cyano group, a di-(lower alkoxy)methyl group or hydroxymethyl group whose hydroxyl group may be protected.

In this method, a phenylacetic acid ester optionally having a substituent can be converted to a carboxylic acid derivative by introducing a —$(CH_2)$m-$R^7$ group to the methylene group of the phenylacetic acid compound and then lower alkylating or lower cycloalkylating the product, or by first lower alkylating or lower cycloalkylating the methylene group and then introducing a —$(CH_2)$m-$R^7$ group thereto. Converting this to a nitrile by a conventional method can give rise to the nitrile ester compound of the present invention. This can be further converted into the nitrile carboxylic acid compound or nitrile alcohol compound of the present invention by a conventional method.

(8) Method Using Phenylacetic Acid Derivative as a Starting Material

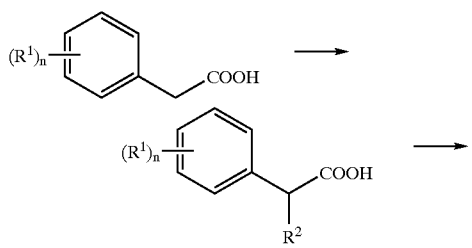

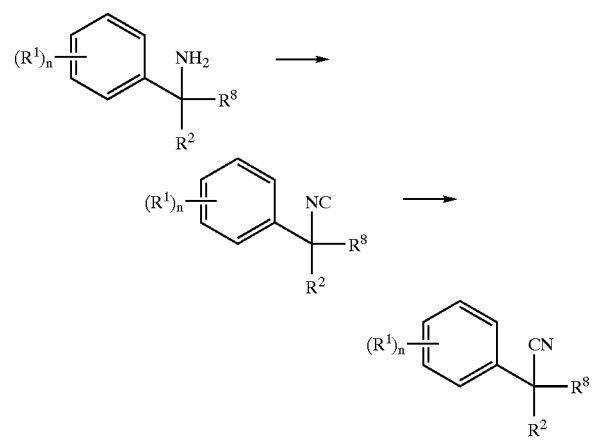

wherein $R^1$, $R^2$ and n have the same meanings as described above.

Lower alkylating or lower cycloalkylating the methylene group of phenylacetic acid optionally having a substituent, reacting the product with allylamine ($CH_2$=$CHCH_2NH_2$) to give a phenylacetamide derivative, and subjecting it to allyl rearrangement and dehydration in accordance with Tet. Lett., 32(2), 179–182, 1991 etc. can give rise to an olefin derivative. Treating this in the same manner as in 6-1) above can give rise to the nitrile carboxylic acid compound of the present invention.

(9) Method Using Benzylaminie Derivative as a Starting Material wherein $R^1$, $R^2$ and n have the same meanings as described above; and $R^8$ means an allyl group, a lower alkyl group or vinyl group.

Converting a benzylamine derivative into a benzyl isocyanide derivative in accordance with Chem. Ber., 125(2), 525–531, 1992. etc., and then subjecting it to rearrangement, can give rise to a benzyl nitrile derivative.

Treating the compound by a conventional method can give rise to the nitrile carboxylic acid compound according to the present invention.

Here, the benzylamine derivative specifically includes, for example, the following compounds.

1) α-Allyl-α-isobutylbenzylamine
2) α-Propyl-α-isobutylbenzylamine
3) α-Vinyl -α-isobutylbenzylamine Note that the benzylamine derivatives mentioned above can be produced, for example, by the following method.

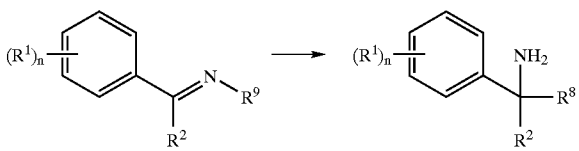

wherein $R^1$, $R^2$, $R^8$ and n have the same meanings as described above; and $R^9$ means a lower alkylsulfonyl group, a lower alkylsulfinyl group, an arylsulfonyl group whose phenyl group may be substituted or an arylsulfinyl group whose phenyl group may be substituted.

The benzylamine forms can be synthesized by reacting an N-substituted phenylimine derivative with allylsilane, Grignard reagent, alkyllithium, arylaluminum, arylborane or metal enolate in accordance with the literature such as J. Org. Chem., 56(1), 4–6, 1991, Synth. Commun., 27(15), 2601–2614, 1997, Synth. Commun. , 20(16), 2409–2416, 1990, J. Am. Chem. Soc., 119, 9913–9914, 1997, J. Am. Chem. Soc., 121, 268–269, 1999, and J. Org. Chem., 64, 12–13, 1999.

The N-substituted phenylimine derivative may include, for example, the following compounds.

1) N-(p-Toluenesulfonyl)phenylisobutanimine $(C_6H_5)(i-C_3H_7)C=NSO_2(p-CH_3C_6H_4)$
2) N-(p-Toluenesulfinyl)phenylisobutanimine $(C_6H_5)(i-C_3H_7)C=NSO (p-CH_3C_6H_4)$
3) N-(t-Butylsulfinyl)phenylisobutanimine $(C_6H_5)(i-C_3H_7)C=NSO (t-C_4H_9)$ In the case where two $R^1$s combine to form a hetero ring, nitrile compound can be produced from known benzimidazole-5-carboxylic acid or the like as a starting material, by a known method and the present invention in combination.

Subsequently, the following Examples are presented in order to explain the present invention in detail. Of course, the present invention should not be limited thereto.

EXAMPLES

Example 1

Synthesis of 4-cyano-5-methyl-4-phenylhexanoic Acid

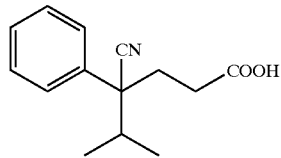

In tetrahydrofuran (1,000 ml) were dissolved 100 g (0.630 mol) of 3-methyl-2-phenylbutanenitrile synthesized in accordance with GB-776,705, BE-529,384, J.O.C., 24, 1561–3, 1959 or the like and 69.2 g (0.690 mol) of ethyl acrylate. To this was added 10.6 g (94.2 mmol) of potassium t-butoxide portionwise at room temperature. During this, heat generation continued. After stirring for 2 hours, brine (100 ml) and SN HCl (150 ml) were successively added thereto and the mixture was extracted with ether (1,000 ml). The organic layer was successively washed with brine (500 ml) and water (500 ml), and then dried over anhydrous magnesium sulfate. The solvent was evaporated, to give 166 g of ethyl 4-cyano-5-methyl-4-phenyl hexanoate as a colorless oil. This was used in the subsequent reaction without purification.

Ethyl 4-cyano-5-methyl-4-phenylhexanoate $^1$H-NMR (400 MHz, CDCl$_3$); δ(ppm) 0.79 (d, J=6.78 Hz, 3H), 1.20 (t, J=7.14 Hz, 3H), 1.23 (d, J=6.59 Hz, 3H), 1.89–2.00 (m, 1H), 2.10–2.26 (m, 2H), 2.34–2.56 (m, 2H), 3.98–4.13 (m, 2H), 7.29–7.42 (m, 5H).

In tetrhydrofuran (500 ml) was dissolved the above ester (166 g). To the mixture was added 5N NaOH (250 ml), followed by stirring. After 3 minutes, tetrahydrofuran (500 ml) was added, and after 3 hours, 5N NaOH (100 ml) was added thereto.

The mixture was further stirred for 17 hours. Toluene (1,000 ml) and water (1,000 ml) were added to the reaction mixture. The aqueous layer was further washed with toluene (500 ml), followed by adding 5N HCl (500 ml) thereto to adjust the pH thereof to 1–2. The mixture was extracted with ethyl acetate (2,000 ml). The organic layer was washed with brine, and then dried over anhydrous magnesium sulfate. The solvent was evaporated, to give 139 g of the title compound as an orange oil. The product was purified by silica gel column chromatography (hexane/ethyl acetate system), to give the title compound as white crystals.

Melting point; 82–84° C.

$^1$H-NMR (400 MHz, CDCl$_3$); δ(ppm) 0.79 (d, J=6.78 Hz, 3H), 1.23 (d, J=6.59 Hz, 3H), 1.94–2.06 (m, 1H), 2.08–2.23 (m, 2H) 2.40–2.55 (m, 2H), 7.29–7.42 (m, 5H) ESI-MS; 230 (M–H)

Example 2

Synthesis of 4-cyano-5-methyl-4-phenylhexanol

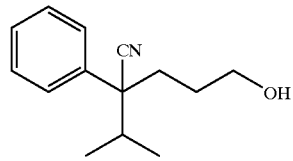

A 4-cyano-5-methyl-4-phenylhexanoic acid (500 mg, 2.16 mmol)/tetrahydrofuran (3.84 ml) solution was slowly added dropwise into a 1M-borane tetrahydrofuran complex/tetrahydrofuran solution (2.70 ml, 2.70 mmol) cooled to −25° C., while keeping the bulk temperature at −15° C. or less. After the completion of the dropwise addition, the bulk temperature was elevated to room temperature. After the completion of the reaction, it was cooled again and methanol (0.33 ml) was added dropwise thereinto. Further, a saturated aqueous sodium hydrogen carbonate solution (200 ml) was added thereinto, followed by extracting with ethyl acetate. The organic layer was successively washed with water, brine and saturated aqueous sodium hydrogen carbonate, followed by drying over magnesium sulfate and evaporating the solvent. The residue was purified by 20 g of Cromatorex NH silica gel (ethyl acetate/hexane system), to give the title compound as a colorless highly viscous oil (426 mg, 1.96 mmol, yield: 90.8%).

$^1$H-NMR (400 MHz, CDCl$_3$); δ(ppm) 0.79 (d, J=6.78 Hz, 3H), 1.21 (d, J=6.78 Hz, 3H), 1.20–1.32 (m, 1H), 1.73–1.83 (m 1H), 1.93–2.06 (m, 1H), 2.08–2.18 (m, 1H), 2.19–2.29 (m, 1H), 3.55–3.64 (m, 2H), 7.26–7.42 (m, 5H). EI-MS; 217 (M$^+$)

Example 3

Synthesis of 4-cyano-5-methyl -4-pehnylhexanol

In tetrahydrofuran (250 ml) was dissolved free carboxylic acid (15.0 g, 64.9 mmol), followed by the dropwise addition of N,N-dimethylformamide (3 drops) with Pasteur pipette. Then, the mixture was ice-cooled. After adding dropwise oxalyl chloride (6.22 ml, 71.3 mmol) thereinto, the resulting mixture was returned to room temperature and stirred for 1 hour. After evaporating the reaction solvent, tetrahydrofuran (150 ml) was added thereto and the mixture was ice-cooled again. After adding methanol (26.3 ml) and triethylamine (10.4 ml, 71.3 mmol), and further methanol (100 ml) thereto, the mixture was elevated to room temperature and stirred for 2 hours. After completion of the reaction, the reaction mixture was extracted with ether, washed with saturated aqueous hydrogen carbonate solution and brine, and dried over magnesium sulfate. The solvent was evaporated, and the resulting residue was purified by silica gel column chromatography (hexane/ethyl acetate system), to give methyl 4-cyano-5-methyl-4-phenylhexanoate as a pale yellow oil (14.8 g, 60.3 mmol, 92.9%).

Methyl 4-cyano-5-methyl-4-phenylhexanoate $^1$H-NMR (400 MHz, CDCl$_3$); δ(ppm) 0.79 (d, J=6.59 Hz, 3H), 1.23 (d, J=6.59 Hz, 3H), 1.91–2.01 (m, 1H), 2.11–2.25 (m, 2H), 2.36–2.55 (m, 2H) 3.61 (s, 3H), 7.26–7.42 (m, 5H).

The above methyl ester form (14.7 g, 59.9 mmol) was dissolved in tetrahydrofuran (200 ml), followed by cooling to −30 to −40° C. After adding dropwise a 1M-lithium aluminum hydride/tetrahydrofuran solution (40 ml) thereinto, the bulk temperature was elevated to 5° C. over 1 hour. After the completion of the reaction, it was cooled again. Water (1.50 ml), 5N sodium hydroxide (1.50 ml) and water (4.50 ml) were successively added thereto, followed by filtering through Celite. The resulting filtrate was evaporated, to give the title compound as a colorless highly viscous oil (11.9 g, 54.9 mmol, yield: 91.7%).

Example 4

Synthesis of 1-[(4-cyano-5-methyl-4-phenyl)hexyl]-4-[2-(4-fluorophenoxy)ethyl]piperazine

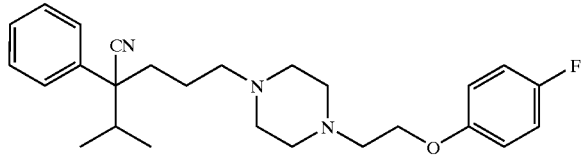

4-Cyano-5-methyl-4-phenylhexanol (197 mg, 0.91 mmol) and triethylamine (0.27 ml, 1.91 mmol) were dissolved in acetonitrile (5 ml), and the solution was cooled to the bulk temperature of 0° C. Methanesulfonyl chloride (1.00 ml, 0.08 mmol) was added dropwise thereinto, and the mixture was elevated to room temperature. After confirming the disappearance of the starting material, 1-[2-(4-fluorophenoxy)ethyl]piperazine (224 mg, 1.00 mmol) and of sodium iodide (682 mg, 4.55 mmol) were successively added thereto at room temperature. The sodium iodide remaining on the wall of the reactor was washed with acetonitrile (2 ml) Thereafter, the mixture was heated to the bulk temperature of about 55° C. After completion of the reaction, it was left to cool to room temperature. To the reaction mixture were added ethyl acetate, water and 0.4 N aqueous sodium hydroxide solution, and the organic layer was washed with brine and then dried over magnesium sulfate, followed by evaporation. The residue was purified by Cromatorex NH silica gel (ethyl acetate/hexane system), to give 326 mg (0.77 mmol) of the titled compound as a pale yellow oil (yield: 84.7%).

$^1$H-NMR (400 MHz, CDCl$_3$); δ(ppm) 0.77 (d, J=6.8 Hz, 3H), 1.05–1.17 (m, 1H), 1.20 (d, J=6.8 Hz, 3H), 1.50–1.60 (m, 1H), 1.88 (dt, J=4.4 Hz, 12.4 Hz, 1H), 2.06–2.19 (m, 2H), 2.24–2.30 (m, 2H), 2.30–2.43 (m, 4H), 2.46–2.62 (m, 4H), 2.77 (t, J=5.8 Hz, 2H), 4.04 (t, J=5.8 Hz, 2H), 6.80–6.85 (m, 2H), 6.91–6.99 (m, 2H), 7.25–7.32 (m, 1H), 7.32–7.40 (m, 4H). ESI-MS; 424 (MH$^+$)

What is claimed is:

1. A nitrile compound represented by the following formula (I):

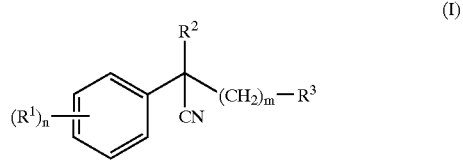

wherein

R$^1$s are the same as or different from each other and each means hydrogen atom, a halogen atom, hydroxyl group, a lower alkyl group, a lower cycloalkyl group, a lower alkoxy group, a lower alkoxyalkoxy group, a halogenated lower alkyl group, a hydroxy-lower alkyl group, a cyano-lower alkyl group, a halogenated lower alkoxy group, a hydroxy-lower alkoxy group, a cyano-lower alkoxy group, a lower acyl group, nitro group, an optionally substituted amino group, an optionally substituted carbamoyl group, an optionally substituted sulfamoyl group, mercapto group or a lower alkylthio group;

R$^2$ means a lower alkyl group or a lower cycloalkyl group, and two R$^1$s may combine to form an aliphatic ring, an aromatic ring, a hetero ring or an alkylenedioxy ring;

n means 0 or an integer of from 1 to 5;

m means an integer of from 1 to 6; and

R$^3$ means carboxyl group, a lower alkoxycarbonyl group, a phenyloxycarbonyl group optionally having a substituent, a phenyl-lower alkylenyl group optionally having a substituent, or hydroxymethyl group;

with the proviso that the following nitrile compounds are excluded:

wherein R$^1$ is a halogen, R$^2$ is a lower alkyl, n is 0 or 1 and R$^3$ is a phenyl-lower alkylenyl optionally having a substituent;

wherein R$^1$ is a lower alkyl, a lower alkoxy, hydrogen atom, a halogen atom, a halogenated lower alkyl, or two R$^1$'s form an alkylenedioxy ring, R$^2$ is isopropyl, R$^3$ is a carboxyl or hydroxymethyl, m is 2 and n is an integer of 1 to 3;

wherein R$^1$ is hydrogen atom, a halogen atom, a lower alkyl or a lower alkoxy, R$^2$ is methyl, m is 1, n is 0, 1 or 2;

wherein R$^1$ is hydroxy or mercapto, n is 1, R$^2$ is lower alkyl, R$^3$ is a phenyl-(1–4C)alkyl;

wherein R$^1$ is hydrogen atom, nitro, a lower alkoxy, or an amino optionally having a substituent, or two R$^1$'s form an alkylenedioxy ring, R$^2$ is a lower alkyl, R$^3$ is a carboxyl or a lower alkoxycarbonyl, m is 2 and n=1; and wherein R$^1$ is a lower alkoxy, hydroxyl, a halogen atom, a halogenated lower alkyl, a lower alkylthio, a carbamoyl optionally having a substituent or an amino optionally having a substituent, R$^2$ is a lower alkyl, R$^3$ is a carboxylic acid, m is 2, and n is 1, 2 or 3.

2. The nitrile compound according to claim 1, which is selected from the following compounds:

(1) 4-cyano-5-methyl-4-phenylhexanoic acid,
(2) methyl 4-cyano-5-methyl-4-phenylhexanoate,
(3) ethyl 4-cyano-5-methyl-4-phenylhexanoate,
(4) 4-cyano-5-methyl-4-phenylhexanol,
(5) 4-cyano-5-methyl-4-(4-methoxyphenyl)hexanoic acid,
(6) 4-cyano-5-methyl-4-(3,4-dimethoxyphenyl)hexanoic acid,
(7) 4-cyano-5-methyl-4-(3,4,5-trimethoxyphenyl)hexanoic acid,
(8) 4-cyano-5-methyl-4-(4-chlorophenyl)hexanoic acid,
(9) 4-cyano-5-methyl-4-(3,4-dichlorophenyl)hexanoic acid,
(10) 4-cyano-5-methyl-4-(3,4,5-trichlorophenyl)hexanoic acid,
(11) 4-cyano-5-methyl-4-(2-trifluoromethylphenyl)hexanoic acid,
(12) 4-cyano-5-methyl-4-(3-trifluoromethylphenyl)hexanoic acid,
(13) 4-cyano-5-methyl-4-(4-trifluoromethylphenyl)hexanoic acid,
(14) 4-cyano-5-methyl-4-(3-sulfamoyl-4-methoxyphenyl)-hexanoic acid,
(15) 4-cyano-5-methyl-4-(2-fluorophenyl)hexanoic acid,
(16) 4-cyano-5-methyl-4-(3-fluorophenyl)hexanoic acid,
(17) 4-cyano-5-methyl-4-(4-fluorophenyl)hexanoic acid,
(18) 4-cyano-5-methyl-4-(2-cyanophenyl)hexanoic acid,
(19) 4-cyano-5-methyl-4-(3-cyanophenyl)hexanoic acid,
(20) 4-cyano-5-methyl-4-(4-cyanophenyl)hexanoic acid,
(21) 4-cyano-5-methyl-4-(2-chlorophenyl)hexanoic acid,
(22) 4-cyano-5-methyl-4-(3-chlorophenyl)hexanoic acid,
(23) 4-cyano-5-methyl-1-4-(2-bromophenyl)hexanoic acid,
(24) 4-cyano-5-methyl-4-(3-bromophenyl)hexanoic acid, and
(25) 4-cyano-5-methyl-4-(4-bromophenyl)hexanoic acid.

3. The nitrile compound according to claim 1, wherein n equals 1 to 5 and $R^1$'s are the same as or different from each other and each means methoxy, chloro, fluoro, bromo, or cyano.

4. The nitrile compound according to claim 1, wherein m equals 2.

5. The nitrile compound according to claim 1, wherein $R^3$ equals carboxyl or lower alkoxy carbonyl.

6. The nitrile compound of according to claim 1, wherein $R^2$ equals branched alkyl.

7. The nitrile compound according to claim 6, wherein the branched alkyl is at least one selected from the group consisting of i-propyl group, i-butyl group, t-butyl group, i-pentyl group, neopentyl group, 1-methylpropyl group, 1-methylbutyl group and 2-methylbutyl group.

8. A process for synthesizing 1-[(4-cyano-5-methyl-4-phenyl)hexyl]-4-[2-(4-fluorophenoxy)ethyl]piperazine comprising:
reducing 4-cyano-5-methyl-4-phenylhexanoic acid with a borane tetrahydrofuran complex to form 4-cyano-5-methyl-4-phenylhexanoic;
reacting 4-cyano-5-methyl-4-pehnylhexanol with 1-[2-(4-fluorophenoxy)ethyl]piperazine to form 1-[(4-cyano-5-methyl-4-phenyl)hexyl]-4-[2-(4-fluorophenoxy)ethyl]piperazine.

* * * * *

UNITED STATES PATENT AND TRADEMARK OFFICE
CERTIFICATE OF CORRECTION

PATENT NO. : 6,667,412 B1 Page 1 of 1
DATED : December 23, 2003
INVENTOR(S) : Suzuki et al.

It is certified that error appears in the above-identified patent and that said Letters Patent is hereby corrected as shown below:

<u>Column 14,</u>
Line 9, change "tetrhydrofuran" to -- tetrahydrofuran --
Line 64, change "4-cyano-5-methyl-4-pehnylhexanol" to
-- 4-cyano-5-methyl-4-phenylhexanol --

<u>Column 15,</u>
Line 25, change "5°C. over" to -- 5°C over --
Lines 52-53, change "and of sodium iodide" to -- and sodium iodide --

Signed and Sealed this

Eighth Day of June, 2004

JON W. DUDAS
*Acting Director of the United States Patent and Trademark Office*